United States Patent [19]

Felcht

[11] 4,247,488
[45] Jan. 27, 1981

[54] PROCESS FOR THE PREPARATION OF 1-OXOPHOSPHOL-Δ³-ENES

[75] Inventor: Utz-Hellmuth Felcht, Bruchmühlbach, Fed. Rep. of Germany

[73] Assignee: Hoechst Aktiengesellschaft, Frankfurt am Main, Fed. Rep. of Germany

[21] Appl. No.: 49,120

[22] Filed: Jun. 18, 1979

[30] Foreign Application Priority Data

Jun. 19, 1978 [DE] Fed. Rep. of Germany ...... 2826621

[51] Int. Cl.³ .................................................. C07F 9/53
[52] U.S. Cl. ......................................... 568/12; 548/217
[58] Field of Search .................... 260/606.5 P; 548/217

[56] References Cited

U.S. PATENT DOCUMENTS

| | | | |
|---|---|---|---|
| 2,663,736 | 12/1953 | McCormack | 260/606.5 P |
| 2,663,737 | 12/1953 | McCormack | 260/606.5 P |
| 2,663,738 | 12/1953 | McCormack | 260/606.5 P |
| 2,663,739 | 12/1953 | McCormack | 260/606.5 P |
| 3,767,708 | 10/1973 | Smith et al. | 260/606.5 P X |
| 3,931,059 | 1/1976 | Spina et al. | 260/606.5 P X |
| 4,080,385 | 3/1978 | Block | 260/606.5 P |

*Primary Examiner*—Helen M. S. Sneed
*Attorney, Agent, or Firm*—Curtis, Morris & Safford

[57] ABSTRACT

1-Oxophosphol-Δ³-enes are prepared in a one-vessel process by reacting dichlorophosphanes, 2-N-acylaminophenols, organic nitrogen bases which bind hydrogen chloride and dienes in a molar proportion of about 1:1: at least 2:(1-2)in an inert solvent witout isolation of an intermediate stage. The reaction products are used as catalysts in the production of rigid polyurethane foams, as selective metal extraction agents or as growth regulators in plant protection.

7 Claims, No Drawings

PROCESS FOR THE PREPARATION OF 1-OXOPHOSPHOL-Δ³-ENES

1-Oxophosphol-Δ³-enes of the formula I

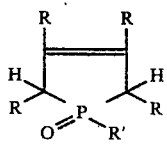

in which the radicals R, which may be identical or different, denote hydrogen, organic radicals and/or halogen and the radicals R' denote organic radicals are industrially interesting compounds, which are used, for example, as catalysts for the preparation of rigid polyurethane foams [compare, for example, German Offenlegungsschrift No. 2,742,275, German Offenlegungsschrift No. 2,552,350 and German Offenlegungsschrift No. 2,245,634], as selective metal extraction agents [compare German Auslegeschrift No. 2,648,782] or as growth regulators in plant protection [compare German Offenlegungsschrift No. 2,503,210].

A number of processes for the preparation of these oxophospholenes have been described. The basic principle of most of the known syntheses is the addition reaction of dihalogenophosphanes II with 1,3-dienes III to give phosphol-Δ³-ene dihalides IV, followed by elimination of the halogen atoms by means of H₂O, ROH and the like [compare equations 1a and 1b]:

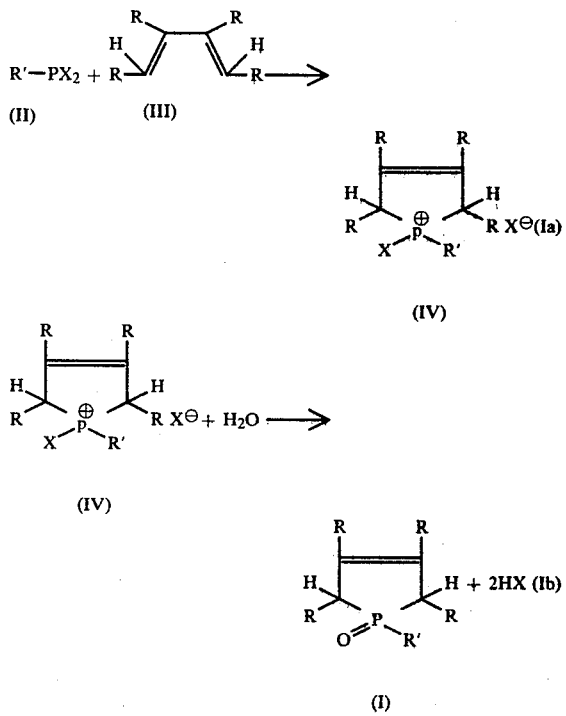

In the formulae, R and R' have the meaning given at the outset, in connection with formula I, and X denotes Cl or Br.

Such a process is described, for example, in U.S. Pat. No. 2,663,737; however, this process is hardly suitable for the industrial manufacture of the oxophospholenes I, because of the time required, which is from several days to a few weeks. To overcome this disadvantage and at the same time to increase the yield, it has more recently been proposed to carry out the reactions in certain particular solvents.

Thus, U.S. Pat. No. 2,855,186 describes the use of nitrohydrocarbons as solvents. The handling of organic nitro compounds, which have an oxidizing action, together with the organodihalophosphanes II, which have a reducing action, represents a substantial safety hazard.

Other authors describe acetic anhydride as a solvent [Soviet Union Patent Specification No. 186,465].

Though the said Soviet Union patent specification speaks of quantitative yields of the desired 1-oxophospholenes, other authors have found, by corresponding repetition experiments, that the organo-dihalogenophosphanes II react rapidly with acetic anhydride, even in the absence of further additives, to give secondary products, so that the process is unsuitable for industrial use [German Patent Specification No. 2,036,173].

The use of oxo-halides of pentavalent phosphorus, especially of phosphorus oxychloride and phosphorus oxybromide, as solvents, described in the latter publication, German Patent Specification No. 2,036,173, however also suffers from disadvantages. In addition to long reaction times (at least 30 hours, according to the examples), it is particularly the fact that the cyclic organo-phosphorus dichlorides IV (see equation Ia) form stable complexes with the solvent, the complexes interfering with hydrolytic working-up according to equation Ib, which is detrimental to the economics of the process. Furthermore, the solvent bonded as a complex is lost during working up.

According to a further process [German Offenlegungsschrift No. 2,606,682], acetyl chloride and other carboxylic acid chlorides are used as solvents. This admittedly produces a slight increase in yield compared to the use of phosphorus oxychloride, but does not achieve a shortening of the reaction time. Furthermore, both solvents are not easy to handle, because of their chemical aggressiveness, and their property of reacting spontaneously with water.

In all processes hitherto mentioned, an additional disadvantage is that the phosphol-Δ³-ene dichlorides IV which constitute the primary products isomerize, in some cases to a considerable extent, on hydrolytic working-up, to give the corresponding oxophosphol-Δ²-enes V [compare equation 2]

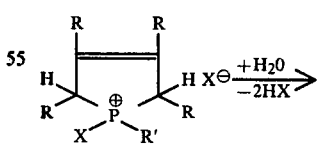

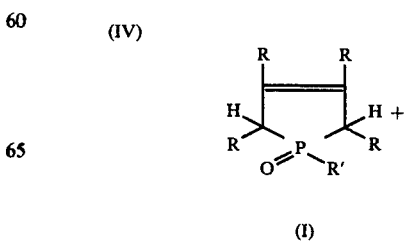

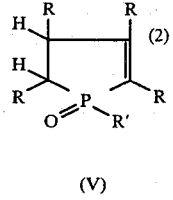

(V)

This isomerization, which takes place relatively easily, is a particular disadvantage if importance is attached to obtaining pure oxophosphol-$\Delta^3$-ene, since the separation of the $\Delta^2$-isomers from the $\Delta^3$-isomers is rather difficult.

Finally, processes are already known in which the desired 1-oxophosphol-$\Delta^3$-enes I are produced from other intermediates than the organodihalogenophosphanes II. Thus, German Offenlegungsschrift No. 2,652,962 describes the reaction of 1-β-chloroalkoxyphospholenes VI with alcohols R'OH to give the 1-oxophospholenes [see equation 3]:

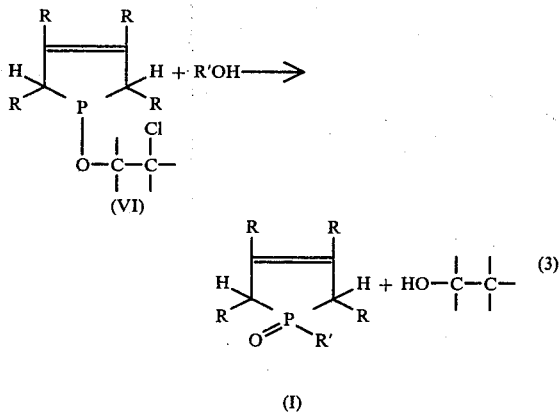

However, in this process the starting compounds VI must first be prepared from the corresponding 1-chlorophospholenes [U.S. Pat. No. 3,767,708]. Since the latter are first obtained by reaction of phosphorus trichloride with 1,3-dienes in the presence of reducing agents, a multi-stage synthesis is involved, which entails considerable expenditure of time and material.

Another synthesis which is based on a multi-stage principle is the reaction, disclosed by M. and A. Pudovik [Izvt. Akad. Nauk. SSR 1974, 964] of 3-acetyl-1,3,2-benzoxazaphospholane VII with isoprene VIII at an elevated temperature to give 3-methyl-1-phenyl-oxophospholene I' [see equation 4c below], since the starting material VII must in turn first be prepared by a two-stage synthesis [corresponding to equations 4a and 4b below] [see M. and A. Pudovik et al., Zh. Obsh. Khim. 44, 1020 (1974)]:

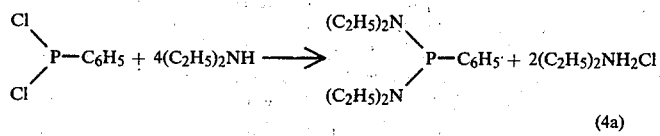

(4a)

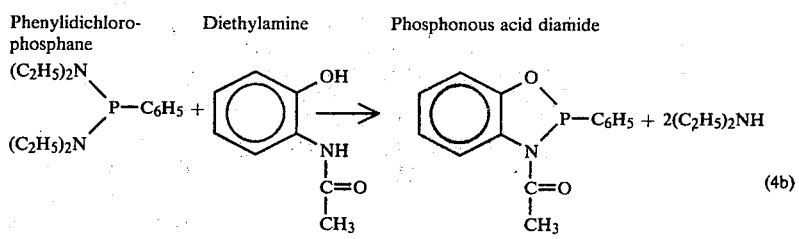

(4b)

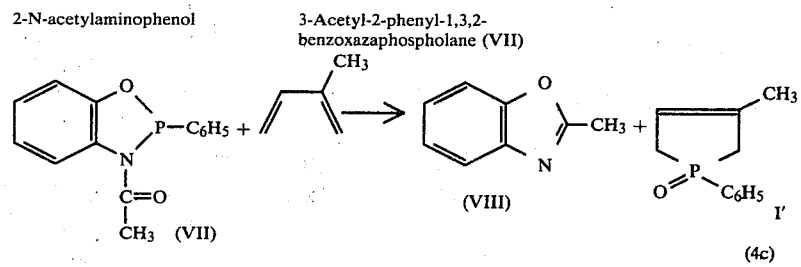

(4c)

The Russian authors mentioned report a yield of 55% of theory for the reaction according to equation 4b and a yield of 87.8% of theory for the reaction according to equation 4c; this means a yield of 3-methyl-1-phenyl-oxophospholene I', relative to the amount of 2-N-acetylaminophenol employed, of about 48.5%. The yield obtained in the reaction according to equation 4a is not included in this calculation, since it is not reported by the Russian authors.

A three-stage synthesis with a yield of less than 50% of theory in the last two stages is uneconomical and therefore unsuitable for carrying out on an industrial scale. However it appears that in this procedure described by the Russian authors mentioned very little or no isomerization of the oxophosphol-$\Delta^3$-ene I', first produced, occurs, so that a separation of isomers, which is difficult to carry out but is necessary, in the case of most of the previously mentioned known processes, in order to obtain pure oxophosphol-$\Delta^3$-ene, need not be carried out in this case.

In an endeavor to provide a simpler and more economical improved process for the preparation of 1-oxophosphol-$\Delta^3$-enes which no longer exhibits the disadvantages of the known processes or at most only retains these disadvantages in a greatly diminished form, it has now been found that the said objective can be achieved in an excellent manner by reacting the starting materials, used in the three-stage process of the above mentioned Russian authors, in a one-vessel process.

Accordingly, the invention relates to a process for the preparation of 1-oxophosphol-$\Delta^3$-enes, starting from dichlorophosphanes, 2-N-acylaminophenols, organic nitrogen bases which bind hydrogen chloride and dienes, wherein dichlorophosphanes, 2-N-acylaminophenols, organic nitrogen bases which bind hydrogen chloride and dienes are reacted in the molar ratio of about 1:1:≧2:(1-2) in a one-stage process in an inert solvent, without isolating an intermediate stage.

In principle, all possible organo-dichlorophosphanes can be used as dichlorophosphanes for the process according to the invention; however, it is preferred to use those dichlorophosphanes of the formula IX

in which $R_2 = (C_1-C_{12})$-alkyl, preferably $(C_1-C_4)$-alkyl, which is optionally substituted by Cl and/or Br, or $R_2$ is cyclopentyl, cyclohexyl, phenyl or naphthyl, which are optionally substituted by Cl, Br, $(C_1-C_4)$-alkyl and/or $(C_1-C_4)$-alkoxy.

Examples of dichlorophosphanes IX are: methyldichlorophosphane, ethyldichlorophosphane, butyldichlorophosphane, chloromethyldichlorophosphane, phenyldichlorophosphane, naphthyldichlorophosphane and the like. They are obtainable in accordance with known processes [K. Sasse in Houben-Weyl, Methoden der orgn. Chemie (Methods of Organic Chemistry), G. Thieme Verlag, Stuttgart 1963, volume 12/1, page 302 et seq.]. Methyldichlorophosphane, ethyldichlorophosphane and phenyldichlorophosphane are particularly preferred.

Suitable 2-N-acylaminophenols are, in principle, all compounds having the 2-N-acylaminophenol basic skeleton; however, preferred compounds are those of the formula X

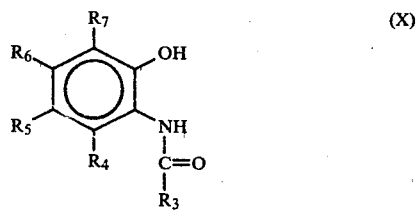

wherein $R_3$ is H, $(C_1-C_{12})$-alkyl, preferably $(C_1-C_4)$-alkyl, which is optionally substituted by Cl and/or Br, or is cyclopentyl, cyclohexyl, phenyl, phenyl or naphthyl which are optionally substituted by Cl, Br, $(C_1-C_4)$-alkyl and/or $(C_1-C_4)$-alkoxy, and $R_4-R_7$ independently of one another are H, $(C_1-C_4)$-alkyl, $(C_1-C_4)$-alkoxy, Cl or Br.

Specific examples of N-acylaminophenols X are compounds such as 2-N-formylaminophenol, 2-N-acetylaminophenol, 2-N-propionylaminophenol, 2-N-butanoylaminophenol, 2-N-benzoylaminophenol, 2-N-acetylamino-2-chlorophenol, 2-N-acetylamino-4-chlorophenol, 2-N-acetylamino-5-chlorophenol, 2-N-acetylamino-6-chlorophenol or the corresponding bromine derivatives, 3-N-acetylamino-4-hydroxytoluene, 4-N-acetylamino-3-hydroxytoluene, 5-N-acetylamino-4-hydroxy-1,2-xylene, 2-N-acetylamino-4-methoxyphenol and the like.

The N-acylaminophenols are prepared in accordance with known methods by acylation, using the corresponding carboxylic acid anhydrides and the free anilines [see, for example, Fierz-David and Kuster, Helv. Chim. Acta 22, 82 (1939), or L. Raiford and C. Creider, J. Am. Chem. Soc. 46, 432 (1924)].

Organic nitrogen bases, which bind hydrogen chloride, which are employed are above all primary, secondary and tertiary amines, especially those with 1-12 C atoms in the molecule. Examples of such amines are triethylamine, N,N-dimethylaniline, pyridine, diethylamine, dimethylamine, N-methylaniline, piperidine, dicyclohexylamine, methylamine, ethylamine, propylamine, butylamine, cyclohexylamine and aniline, triethylamine being particularly preferred.

Suitable dienes are in principle all the possible 1,3-dienes, above all those of the formula XI:

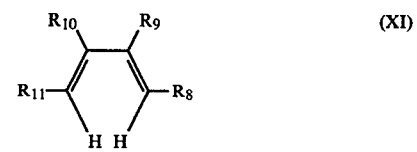

in which $R_8-R_{11}$ are, independently of one another, H or $(C_1-C_{12})$-alkyl, preferably $(C_1-C_4)$-alkyl, which is optionally substituted by chlorine and/or bromine, or cyclopentyl, cyclohexyl, phenyl or naphthyl, which are optionally substituted by Cl, Br, $(C_1-C_4)$-alkyl and/or $(C_1-C_4)$-alkoxy, or Cl or Br.

Specific examples of suitable dienes are butadiene, isoprene, dimethylbutadiene, chloroprene, 1-methylbutadiene and 1-phenylbutadiene; butadiene, isoprene and 2,3-dimethylbutadiene are particularly preferred.

Usable solvents which are inert towards the starting compounds are aliphatic and aromatic hydrocarbons, especially those with 5-8 C atoms, such as, for example, heptane, hexane, pentane or petrol mixtures containing $(C_{5-8})$-aliphatics, benzene, toluene, xylene and the like. Chlorinated hydrocarbons, especially those with 1 or 2 C atoms, such as methylene chloride, chloroform or carbon tetrachloride, dichloroethane or trichloroethane are also used. Inert ethers, especially aliphatic ethers with 4-6 C atoms, such as, for example, tetrahydrofuran, dioxane, diisopropyl ether or diethyl ether, can also be used.

Formally the process according to the invention can be represented by the following equation if dichlorophosphanes of the formula IX, 2-N-acylaminophenols of the formula X and dienes of the formula XI are employed, the organic nitrogen bases, which bind hydrogen chloride, being hereafter represented by the symbol B:

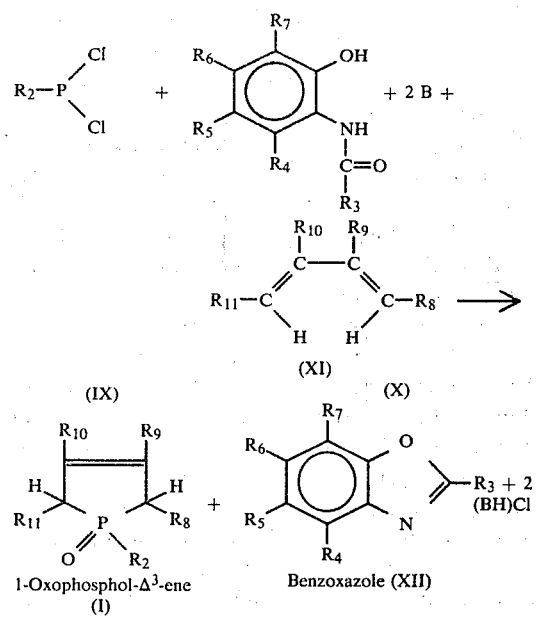

The process according to the invention can be carried out over a relatively broad temperature range. In general, it is carried out at temperatures of about +50° to +200° C., preferably of about +90° to +160° C. The reaction time is between about one and about 10 hours, in general about 3-6 hours.

The process is in general carried out under an inert gas atmosphere. Suitable inert gases are nitrogen, carbon dioxide and argon, but in the case of gaseous or readily volatile dienes, such as, for example, butadiene, it also suffices to flush the gas space in the reaction vessel with an excess of diene.

The ratio of the solvent to the sum of the reactants can be varied within a relatively wide range. In general, a weight ratio of solvent:sum of the reactants of about 1:1 to about 10:1, preferably a ratio of about 2:1 to about 5:1, is used.

In general, the procedure followed is to mix the reactants and heat the mixture, or to pass or drip one of the reactants, preferably—because of its volatility—the 1,3-diene, last of all into the reaction mixture of the other components.

The reaction is in general carried out under pressure, the pressure in the reaction vessel corresponding to the vapor pressure of the volatile components at the particular temperature. Furthermore, polymerization inhibitors in amounts of about 0.1–1% by weight, relative to the total weight of the reaction batch, are in general added to the reaction mixture. The advisability of adding inhibitors, such as, for example, copper stearate, phenothiazine or tert.-butylpyrocatechol when carrying out reactions between organodichlorophosphanes and 1,3-dienes is known [Houben-Weyl, Methoden der org. Chemie (Methods of Organic Chemistry), Georg Thieme Verlag, Stuttgart 1963, volume XIV/1].

After completion of the reaction, the hydrochloride precipitate is next removed by filtration, with or without the use of pressure, or by centrifuging.

After having separated off the salt precipitate, the solution obtained, which contains the reaction products benzoxazole XII and 1-oxophospholene I is freed from solvent by distillation under normal or reduced pressure. The mixture which remains is separated by fractional distillation under reduced pressure.

The resulting benzoxazoles XII are again split, in accordance with known methods, for example by reaction with dilute acids, to give the corresponding N-acylaminophenols X, which can then be employed afresh [Ladenburg, Ber. 9, 1525 (1876)].

The possibility of starting from 4 different starting materials, which it has hitherto only been possible to convert to the corresponding 1-oxophosphol-$\Delta^3$-enes in a three-stage process, and now converting them in a single-stage process, furthermore with substantially higher yields, represents an exceptional advance. In addition, the process is distinguished by the short reaction times which amount to at most about 10 hours. The 1-oxophospholenes obtained are distinguished by a high purity of the isomer, which represents a further important advantage.

The success of the reaction was exceptionally surprising since, within the stated temperature range, 1,3-dienes, on reaction with dichlorophosphanes in inert solvents, will only give cyclic organophosphorus (V) dichlorides, of the type initially designated IV, accompanied by severe resinification. Furthermore, it was surprising that the presence of organic nitrogen bases, such as, for example, triethylamine, does not interfere, though it has been demonstrated that triethylamine interferes with the addition reaction of dichlorophosphanes with 1,3-dienes [see K. Moedritzer, Syn. React. Inorg. Metal-Org. Chem. 5(4), 299 (1975)].

The invention will now be explained in more detail with the aid of the examples which follow.

EXAMPLE 1

0.1 g of Cu stearate, as the inhibitor, and 14.8 ml (0.11 mole) of phenyldichlorophosphane are added successively to 15.1 g (0.11 mole) of 2-N-formylaminophenol, 23 g (0.23 mole) of triethylamine and 150 ml of toluene in a pressure bottle. After cooling the mixture to from 0° to −5° C., 6 g (0.11 mole) of condensed butadiene are added, and the pressure bottle is closed and kept for 6 hours at a bath temperature of 150° C. After cooling, the hydrochloride precipitate is filtered off, the filtrate is concentrated at 30° C./12 mm Hg and the oily residue is fractionated.

The following are obtained successively: 9.0 g (68.8% of theory) of 1,3-benzoxazole of boiling point/1.0 mm Hg: 40°–42° C. and 13.8 g (70.5% of theory) of 1-phenyl-1-oxophosphol-$\Delta^3$-ene, of boiling point/0.5 mm Hg: 134°–137° C., which according to analysis by gas chromatography contains 1.8% of the $\Delta^2$-isomer.

EXAMPLE 2

151 g (1.1 moles) of 2-N-formylaminophenol, 230 g (2.3 moles) of triethylamine, 3.0 of Cu stearate, 3.0 g of tert.-butylpyrocatechol and 2,500 ml of toluene are introduced into a 4 liter enamelled pressure reactor. The reactor is flushed with nitrogen for 10 minutes and 148 ml (1.1 moles) of phenyldichlorophosphane are then added dropwise, whilst stirring. 100 g (1.85 moles) of butadiene from a butadiene cylinder are then introduced as gas, the valves are closed and the reactor is heated up. It is kept for 4 hours at 140° C. followed by 2 hours at 160° C. and is then cooled. Thereafter the reaction mixture is filtered on a pressure filter, the solvent is removed at 50° C./30 mm Hg and the residue is fractionated. The following are obtained successively:

86 g (65.7% of theory) of 1,3-benzoxazole of boiling point/1.4 mm Hg: 50°-52° C., and 169 g (86% of theory) of 1-phenyl-1-oxophosphol-Δ³-ene, of boiling point/1.0 mm Hg: 144°-146° C., which according to analysis by gas chromatography contains 8.5% of the Δ²-isomer.

A comparison of Examples 1 and 2 shows that even a substantial excess of 1,3-diene does not lead to a reduction in yield due to polymeric constituents.

EXAMPLE 3

Analogously to Example 1, 15.1 g (0.11 mole) of 2-N-formylaminophenol, 23 g (0.23 mole) of triethylamine, 150 ml of toluene, 0.1 g of Cu stearate and 14.8 ml (0.11 mole) of phenyldichlorophosphane are reacted with 7.5 g (0.11 mole) of isoprene, and the mixture is worked up.

This gives 8.7 g (66.5% of theory) of 1,3-benzoxazole, of boiling point/1.0 mm Hg: 40°-42° C., and 16.0 g (75.8% of theory) of 3-methyl-1-phenyl-1-oxophosphol-Δ³-ene, of boiling point/1 mm Hg: 153°-155° C., which according to analysis by gas chromatography contains 1.7% of the Δ²-isomer.

EXAMPLE 4

37.7 g (0.275 mole) of 2-N-formylaminophenol, 57.7 g (0.57 mole) of triethylamine, 0.5 g of Cu stearate, 800 ml of toluene and 37.1 ml (0.275 mole) of phenyldichlorophosphane are introduced into a 2 liter steel autoclave equipped with a up- and down-stirrer. 28 g (0.41 mole) of isoprene are added thereto as a single charge and after closing the autoclave the mixture is heated for 6 hours to 140° C. and then additionally for 2 hours at 160° C. After cooling, the contents of the autoclave are filtered on a suction filter, the filtrate, thus freed from the hydrochloride precipitate, is concentrated at 30° C./12 mm Hg, and the oily residue is fractionated.

The following are obtained successively: 26.2 g (80.1% of theory) of 1,3-benzoxazole of boiling point/1.0 mm Hg: 40°-41° C., and 35.3 g (66.9% of theory) of 3-methyl-1-phenyl-1-oxophosphol-Δ³-ene of boiling point/1 mm Hg: 154°-157° C., which according to analysis by gas chromatography contains 9.9% of the Δ²-isomer.

A comparison of Examples 3 and 4 shows that the isomer ratio depends on external parameters, such as the material of the vessel used.

EXAMPLE 5

Analogously to Example 1, 15.1 g (0.11 mole) of 2-N-formylaminophenol, 23 g (0.23 mole) of triethylamine, 100 ml of toluene, 0.1 g of Cu stearate and 10 ml (0.11 mole) of methyldichlorophosphane are reacted with 8 g (0.12 mole) of isoprene, and the mixture is worked up.

This gives 10.6 g (80.9% of theory) of 1,3-benzoxazole of boiling point/0.8 mm Hg: 40° C. and 10.4 g (72.7% of theory) of 1,3-dimethyl-1-oxo-phosphol-Δ³-ene of boiling point/0.3 mm Hg: 85°-87° C., which according to analysis by gas chromatography does not contain any Δ²-isomer.

EXAMPLE 6

151 g (1.1 moles) of 2-N-formylaminophenol, 230 g (2.3 moles) of triethylamine, 3.0 g of Cu stearate, 3.0 g of tert.-butylpyrocatechol and 2,500 ml of toluene are introduced into a 4 liter enamelled pressure reactor. The reactor is flushed with nitrogen for 10 minutes, after which 100 ml (1.1 moles) of methyldichlorophosphane, followed by 100 g (1.5 moles) of isoprene, are introduced dropwise, whilst stirring. After closing the valves, the mixture is heated for 5 hours in stages, namely first for 2 hours at 120° C., then for 2 hours at 140° C. and lastly for 1 hour at 150° C. After cooling, the reaction mixture is filtered on a pressure filter, the solvent is stripped off at 30° C./15 mm Hg and the residue is fractionated.

The following are obtained successively: 92 g (70.3% of theory) of 1,3-benzoxazole of boiling point/1.0 mm Hg: 40°-43° C., and 111 g (77.6% of theory) of 1,3-dimethyl-1-oxophosphol-Δ³-ene of boiling point/1.0 mm Hg: 95°-97° C., which according to analysis by gas chromatography does not contain any Δ²-isomer.

A comparison of Examples 5 and 6 shows that an increase in yield can be achieved by slowly raising the temperature within the range of reaction temperatures.

EXAMPLE 7

151 g (1.1 moles) of 2-N-formylaminophenol, 230 g (2.3 moles) of triethylamine, 3.0 g of Cu stearate, 3.0 g of tert.-butylcatechol and 2,500 ml of toluene are introduced into a 4 liter enamelled pressure reactor. The reactor is flushed with nitrogen for 10 minutes and 100 ml (1.1 moles) of methyldichlorophosphane are then introduced dropwise, whilst stirring. 100 g (1.85 moles) of butadiene are then introduced, as a gas, from a butadiene cylinder, the valves are closed and the reactor is heated for 6 hours in stages, namely first for 2 hours at 120° C., and then for 2 hours at 140° C. and lastly for 2 hours at 150° C. After cooling, the reaction mixture is filtered through a pressure filter, the solvent is stripped off at 30° C./15 mm Hg and the residue is fractionated.

The following are obtained successively: 61 g (61.9% of theory) of 1,3-benzoxazole, of boiling point/1.0 mm Hg: 40°-42° C., and 101 g (79.2% of theory) of 1-methyl-1-oxophosphol-Δ³-ene, of boiling point/1.0 mm Hg: 88°-89° C., which according to analysis by gas chromatography contains 12% of the Δ²-isomer.

EXAMPLE 8

167.4 g (1.1 moles) of 2-N-acetylaminophenol, 230 g (2.3 moles) of triethylamine, 3.0 g of Cu stearate, 3.0 g of tert.-butylpyrocatechol and 2,500 ml of toluene are introduced into a 4 liter enamelled pressure reactor. The reactor is flushed with nitrogen for 10 minutes and 85 g (1.25 moles) of isoprene, followed by 100 ml (1.0 moles) of methyldichlorophosphane are then introduced dropwise, whilst stirring. After closing the valves, the reactor is heated first for 4 hours at 140° C. and then for 1 hour at 150° C. After cooling, and filtering off the hydrochloride precipitate, the solvent is removed at 30° C./15 mm Hg and the residue is fractionated.

The following are obtained successively: 121 g (82.7% of theory) of 2-methyl-1,3-benzoxazole, of boiling point/1.0 mm Hg: 55°-56° C., and 74 g (51.7% of theory) of 1,3-dimethyl-1-oxophosphol-Δ³-ene of boiling point/1.0 mm Hg: 95° C., which according to analysis by gas chromatography does not contain any Δ²-isomer.

EXAMPLE 9

Example 8 is repeated, only reversing the sequence of dropwise addition of isoprene and methyldichlorophosphane. Appropriate working up gives 112 g (76.6% of theory) of 2-methyl-1,3-benzoxazole of boiling point/1.0 mm Hg: 56° C. and 89 g (62.2% of theory) of 1,3-dimethyl-1-oxophosphol-$\Delta^3$-ene of boiling point/1.0 mm Hg: 94°–96° C.

A comparison of Examples 8 and 9 shows that the sequence of addition of the organodichlorophosphane and 1,3-diene reactants to the auxiliary materials is in principle optional, but that by addition of the diene as the last reactant a slight increase in yield can be achieved.

EXAMPLE 10

Analogously to Example 1, 15.1 g (0.11 mole) of 2-N-formylaminophenol, 23 g (0.23 mole) of triethylamine, 150 ml of toluene, 0.1 g of Cu stearate, 14.8 ml (0.11 mole) of phenyldichlorophosphane and 10.0 g (1.2 moles) of 2,3-dimethylbutadiene are reacted in a pressure bottle, and worked up.

This gives 8.4 g (64.2% of theory) of 1,3-benzoxazole of boiling point/1.0 mm Hg: 42° C., and 14.2 g (62.7% of theory) of 2,3-dimethyl-1-phenyl-1-oxophosphol-$\Delta^3$-ene of boiling point/1.0 mm Hg: 161°–164° C., which according to analysis by gas chromatography does not contain any $\Delta^2$-isomer.

I claim:

1. A process for the preparation of a 1-oxophosphol-$\Delta^3$-ene, starting from a dichlorophosphane of the formula IX

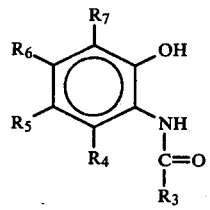

in which $R_2 = (C_1-C_{12})$-alkyl, which is optionally substituted by Cl and/or Br, or $R_2$ is cyclopentyl, cyclohexyl, phenyl or naphthyl, which are optionally substituted by Cl, Br, $(C_1-C_4)$-alkyl and/or $(C_1-C_4)$-alkoxy; 2-N-acylaminophenol of the formula X

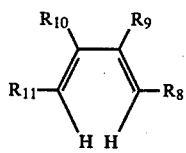

wherein $R_3$ is H, $(C_1-C_{12})$-alkyl, which is optionally substituted by Cl and/or Br, or is cyclopentyl, cyclohexyl, phenyl or naphthyl which are optionally substituted by Cl, Br, $(C_1-C_4)$-alkyl and/or $(C_1-C_4)$-alkoxy, and $R_4-R_7$ independently of one another are H, $(C_1-C_4)$-alkyl, $(C_1-C_4)$-alkoxy, Cl or Br; an organic nitrogen base which binds hydrogen chloride wherein said nitrogen base is a primary, secondary and/or tertiary amine with 1 to 12 C atoms in the molecule and a diene wherein the diene is a compound of the formula XI

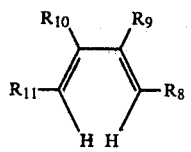

in which $R_8-R_{11}$ are, independently of one another, H or $(C_1-C_{12})$-alkyl, which is optionally substituted by chlorine and/or bromine, or cyclopentyl, cyclohexyl, phenyl or naphthyl, which are optionally substituted by Cl, Br, $(C_1-C_4)$-alkyl and/or $(C_1-C_4)$-alkoxy, or Cl or Br; wherein said dichlorophosphane, 2-N-acylaminophenol, organic nitrogen base which binds hydrogen chloride and a diene are reacted, at a temperature between 50° to 200° C., in the molar ratio of about 1:1: at least about 2:(1–2) in a one-stage process in an inert solvent, without isolating an intermediate stage and at a pressure corresponding to in-situ pressure corresponding at said temperature.

2. The process as defined in claim 1, wherein the dichlorophosphane used is a compound of the formula IX

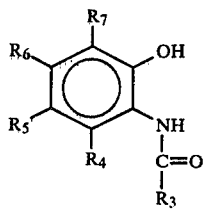

in which $R_2$ is a $C_1-C_4$-alkyl, which is optionally substituted by Cl and/or Br, or $R_2$ is cyclopentyl, cyclohexyl, phenyl or naphthyl, which are optionally substituted by Cl, Br, $(C_1-C_4)$-alkyl and/or $(C_1-C_4)$ alkoxy.

3. The process as defined in any one of claims 1 or 2, wherein the 2-N-acylaminophenol used is a compound of the formula X

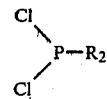

wherein $R_3$ is H, $(C_1-C_4)$-alkyl, which is optionally substituted by Cl and/or Br, or is cyclopentyl, cyclohexyl, phenyl, or naphthyl which are optionally substituted by Cl, Br, $(C_1-C_4)$-alkyl and/or $(C_1-C_4)$-alkoxy, and $R_4-R_7$ independently of one another are H, $(C_1-C_4)$-alkyl, $(C_1-C_4)$-alkoxy, Cl or Br.

4. The process as defined in any one of claims 1 to 3, wherein primary, secondary and/or tertiary amines with 1 to 12 C atoms in the molecular are used as an organic nitrogen base which binds hydrogen chloride.

5. The process as defined in any one of claims 1 to 3, wherein the diene is a compound of the formula XI

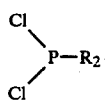

in which $R_8-R_{11}$ are, independently of one another, H or $(C_1-C_4)$-alkyl, which is optionally substituted by chlorine and/or bromine, or cyclopentyl, cyclohexyl, phenyl or naphthyl, which are optionally substituted by Cl, Br, $(C_1-C_4)$-alkyl and/or $(C_1-C_4)$-alkoxy, or Cl or Br.

6. The process as defined in any one of claims 1 to 5, wherein the inert solvents used are aliphatic and/or aromatic hydrocarbons with 5 to 8 C atoms, chlorohydrocarbons with 1 or 2 C atoms and/or aliphatic ethers with 4 to 6 C atoms.

7. The process as defined in any one of claim 1 to 6, wherein the reaction is carried out at temperatures of about 90° to 160° C.

* * * * *